US00RE38058E

(19) United States
(12) Reissued Patent
Fallin

(10) Patent Number: US RE38,058 E
(45) Date of Reissued Patent: Apr. 1, 2003

(54) MILL AND GUIDE APPARATUS FOR PREPARATION OF A HIP PROSTHESIS

(75) Inventor: Thomas W. Fallin, Hyde Park, UT (US)

(73) Assignee: Smith & Nephew, Inc., Memphis, TN (US)

(21) Appl. No.: 08/582,025

(22) Filed: Jan. 2, 1996

Related U.S. Patent Documents

Reissue of:
(64) Patent No.: 5,047,033
Issued: Sep. 10, 1991
Appl. No.: 07/476,172
Filed: Feb. 7, 1990

U.S. Applications:

(63) Continuation of application No. 08/120,034, filed on Sep. 10, 1993, which is a continuation-in-part of application No. 07/308,205, filed on Feb. 8, 1989, now Pat. No. 4,995,883.

(51) Int. Cl.[7] ..... A61F 5/04
(52) U.S. Cl. ..... 606/87
(58) Field of Search ..... 606/79, 80, 84, 606/85, 86, 87; 632/22.11, 22.12, 22.4

(56) References Cited

U.S. PATENT DOCUMENTS 4,399,813 A * 8/1983 Barber ..... 606/100
4,515,154 A * 5/1985 Leonard ..... 433/73
4,722,331 A * 2/1988 Fox ..... 606/80
4,738,256 A * 4/1988 Freeman et al. ..... 606/87
4,777,942 A * 10/1988 Frey et al. ..... 409/178

* cited by examiner

*Primary Examiner*—David J. Isabella
(74) *Attorney, Agent, or Firm*—Pravel, Hewitt, Kimball & Krieger

(57) ABSTRACT

A guide apparatus for preparing the femur of a patient with a rotary mill to receive a femoral hip prosthesis includes a V-shaped guide body having a lower end base portion adapted to extend into the intermedullary canal of the femur and an upper end portion comprised of at least two spaced apart struts so that the overall guide body had a configuration substantially the same as the prosthesis body sought to be implanted in the patient. The lower end of the guide body base provides one or more hemispherical receptacles for holding the hemispherical end portion of a spinning mill bit. A preferably removable transverse guide rail has connection pins at one end portion thereof for forming a connection with the upper end of the guide body at one of the struts, the arm having a curved surface that is adapted to guide the mill bit during preparation of the intermedullary canal of the patient's femur for receiving a hip prosthesis thereafter.

21 Claims, 3 Drawing Sheets

MILL AND GUIDE APPARATUS FOR PREPARATION OF A HIP PROSTHESIS

Matter enclosed in heavy brackets [ ] appears in the original patent but forms no part of this reissue specification; matter printed in italics indicates the additions made by reissue.

CROSS REFERENCE TO RELATED APPLICATIONS

*This is a continuation of application Ser. No. 08/120,034, filed on Sep. 10, 1993* [This] *which* is a continuation-in-part of U.S. patent application Ser. No. 07/308,205, filed 02/08/89 now U.S. Pat. No. 4,995,883.

BACKGROUND OF THE INVENTION

1. Field of the Invention

The present invention relates to a modular hip prosthesis system wherein various custom, selected component parts of an implant can be selected during the surgical procedure and a corresponding mill or rotary reamer guide selected to prepare the femur so that the implant can be custom fitted to a patient.

2. General Background

Increasingly, surgeons want to be able to custom fit femoral prostheses to patients. Instead of having to choose a properly sized prosthesis from a group of pre-formed implants, it would be advantageous to have a basic design which can be modified with various component parts. This would eliminate the need to maintain a large inventory and would provide better fitting implants. In addition, the femur of each patient can differ slightly so that some cutting and/or reaming of the intermedullary cavity is desireable for properly preparing the femur to receive the selected prosthesis.

Custom fitted implants are particularly important in revision cases where an implant has to be removed and replaced since old cement must be removed and bone resorption occurs in many cases. Unpredictable, proximal and/or distal bone loss of deformity often occurs which must be accommodated by the replacement prosthesis.

For initial implants, basic variations in patient anatomy are often confronted by the surgeon. Variations in intramedullary canal diameter can also occur, which if not accompanied by a properly sized implant, can result in distal toggle.

In short, it is difficult, of not impossible, to predict the exact shape of a hip implant which is suitable for all patients. Since it is impractical and would be prohibitively expensive to maintain an inventory of implants for most patients, compromises must sometimes be made in supplying implants which fit reasonably well but could be improved upon.

Several hip prostheses are known which are formed of replaceable or interchangeable component parts.

U.S. Pat. No. 3,641,590 entitled "Acetabular Replacement Prosthesis and Method of Assembling" issued to Michele discloses a selective individualized technique for acetabulum socket replacement per se, or in conjunction with a hip replacement prosthesis (referring to the Michele U.S. Pat. No. 3,228,393) for a total hip replacement, designed for all ages including the very young. A selective anchorage for a cup prosthesis of a size selected from the limited number of differently sized cups is made available. Anchorage of the acetabular socket replacement conforms to variations in dimensions, shapes and positions of the (medullary) canals of the acetabulum pelvis of the individual patient and includes at least two elongated and convergent or divergent fasteners.

A removable collar of low modular of elasticity material is shown in U.S. Pat. No. 4,012,796 entitled "Interpositioning Collar For Prosthetic Bone Insert" issued to Weisman et al. The collar is interpositioned between a collar of a metal prosthetic hip stem implanted in the intramedullary canal of the femur and the adjacent calcar or outer edge of the bone. A flange depends from the insert between the upper portion of the stem and the inner wall of the bone. The interpositioned collar is either a full elongated tapered O-shape or it is open on one side of a tapered U-shape.

U.S. Pat. No. 4,404,691 entitled "Modular Prosthesis Assembly" issued to Buning et al., provides a modular hip prosthesis assembly for replacement of at least part of a joint and part of a bone shaft including a mounting component provided with a connection portion and at least two joint components of similar shape but different dimensions and which can be connected alternatively to the mounting component, each of the joint components having an engagement portion and a connection part adapted for connection to the connection portion of the mounting component, the joint components each providing part of a bone shaft and part of a joint which can cooperate with an appropriate part of a natural or artificial joint.

U.S. Pat. No. 4,578,081 entitled "Bone Prosthesis" issued to Harder et al., discloses a bone prosthesis comprising at least one joint component replacing a natural joint half, which is provided with a shank adapted to be connected to the bone, wherein a set of joint components is provided, and the shank is designed as a bone replacement member, with a connection portion provided adapted to be connected to the bone at one end and at the other end to the shank. One of the components is a hip prosthesis with a rounded head and a hollowed hip component that connects to elongated mounting components. In another hip prosthesis embodiment, a neck with a cone shape receives a suitable joint head with an inner cone.

A femoral component for hip prosthesis is shown in U.S. Pat. No. 4,608,055 issued to Morrey et al., the prosthesis disclosed in the '055 patent includes a stem portion and a combined integral head and neck portion. The stem portion includes a proximal portion and a distal portion which are angular related with a respect to one another and with the proximal portion including a recess formed therein for receipt of a tapered portion of the head and neck component. The head and neck component includes a substantially part spherical head portion attached to a neck portion and a tapered portion angularly attached to the neck portion via a basilar neck portion with the tapered portion being adapted to be permanently inserted into the recess portion of the proximal end of the above described stem portion. The stem portion includes a plurality of recesses on the periphery and longitudinal extent thereof for receiving fiber metal pads which are provided to allow boney ingrowth therein in order to retain the femoral component permanently installed in the proximal end of the femur.

In U.S. Pat. No. 4,676,797 entitled "Unit for Resection Prosthesis", a resection prosthesis assembly unit includes a head member, an end member and an intermediate member between the head and end members, of which one member is provided with a conical pin and another member is provided with a conical pin and another member is provided with a conical bore. The latter two members are provided with respective first surfaces extends transversely to an insertion direction and which face one another and are spaced apart to define a recess when the two members are connected together. One of the two members is further provided with a second surface extending in the insertion direction, and the recess being provided to receive a wedge insertable into the recess to bear against the first surfaces for forcing the two members apart while the forces exerted by the wedge are absorbed by the first surfaces and the wedge is guided by the second surface.

One type of cutting guide for use with a reamer in preparing the proximal end of the femur for a hip prosthesis is described in U.S. Pat. No. 4,777,942, entitled "Bone Milling Instrument." The '942 patent discloses a milling instrument which is inserted into a medullary cavity and a spindle which is linked to the caliper at an angle. The spindle carries a milling cutter as well as a guide shoe at the distal end which slides within a guideway at the distal end of the caliper. The instrument is able to cut a circular arc corresponding to the boundary line between the spongiosa and cortical tissue in the region of the calcar arc.

SUMMARY OF THE INVENTION

The present invention provides a rotary reamer guide apparatus for preparing the femur for a hip prosthesis which can then be custom fitted to a particular patient by a surgeon prior to surgical insertion of the prosthesis.

The apparatus includes preferably a V-shaped guide body having a lower end base portion that is adapted to extend into the intermedullary canal of the femur during use, with an upper end portion comprised of a pair of spaced apart struts. The lower end of the base includes one or more receptacles for holding the end of a mill or rotary reamer.

In the preferred embodiment, the mill provides at its lower end portion a hemispherical surface and the receptacle comprises a pair of spaced apart hemispherical receptacles, for containing the hemispherical portion of the mill in one of two pre-selected cutting positions for the lower end of the reamer.

A curved, transverse guide rail is provided which attaches at a removable connection with the upper end of the guide body at one of the struts, the guide rail including a cantilevered arm having a curved surface that is adapted to engage and guide the mill during preparation of the intermedullary canal of the patient's femur before receiving a hip prosthesis.

Because the guide rail is removable from the guide body, the present invention provides a modular kit wherein a plurality of different guide rails can be used for creating cuts of different pre-selected configurations in the intermedullary canal. Thus, the surgeon can select a particular guide rail configuration and resultant cut for the intermedullary canal depending upon the particular patient's needs and depending upon a particular selected modular prosthesis that will be implanted.

The guide body preferably defines an envelope having a size and shape that corresponds to the shape of the upper end portion of the prosthesis body so that the guide body and the cut made by the reamer closely corresponds to the actual shape of the prosthesis to be implanted, thus eliminating the problem of a poor fit.

In the preferred embodiment, the guide rail provides a cantilevered arm that extends away from the V-shaped guide body, connecting thereto by means of a removable connection, such as, for example, a pair of spaced apart pins that downwardly extends from the cantilevered arm into sockets provided on the guide body. As an alternate construction, the connection can be in the form of a dove-tail shaped connection member carried by the guide rail, arm and slidably interfacing with a dove-tail shaped recess in the guide body. The guide rail can provide connectors on both the superior and inferior surfaces to that each guide rail can be used to make both anterior and posterior cuts as desired.

BRIEF DESCRIPTION OF THE DRAWINGS:

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 2:
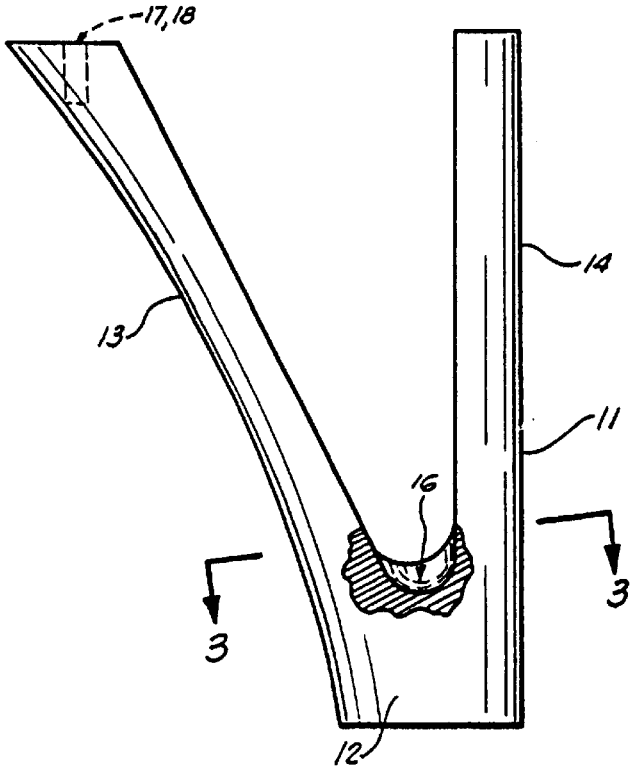
FIG. 2 is a fragmentary side view of the preferred embodiment of the apparatus of the present invention illustrating the guide body.
Figure 1:
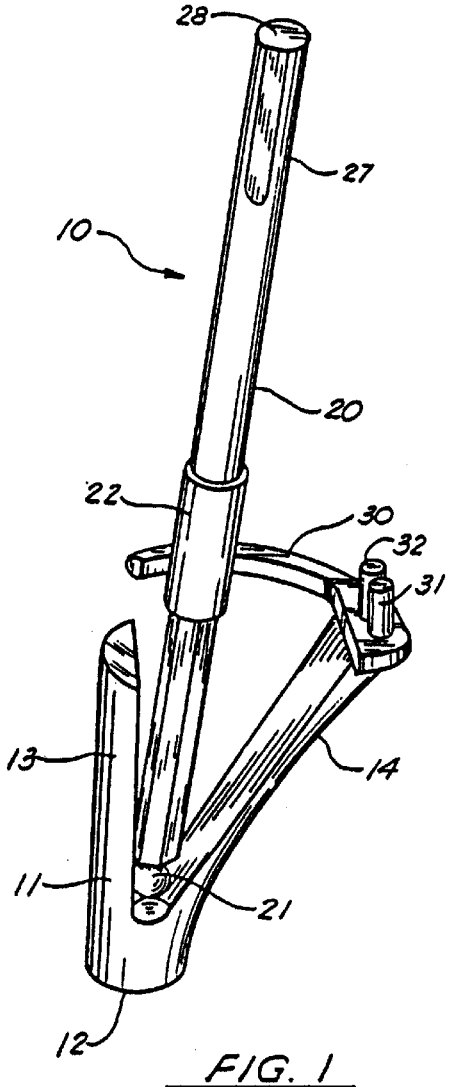
FIG. 1 is a perspective view of the preferred embodiment of the apparatus of the present invention.
Figure 3:
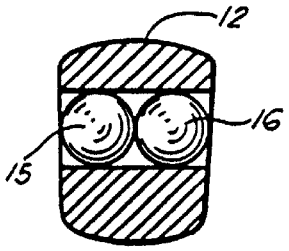
FIG. 3 is a sectional view taken along lines 3—3 of FIG. 2.
Figure 4:
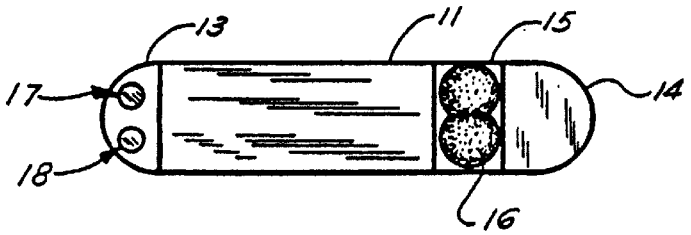
FIG. 4 is a top view of the guide body of FIG. 2.
Figure 7:
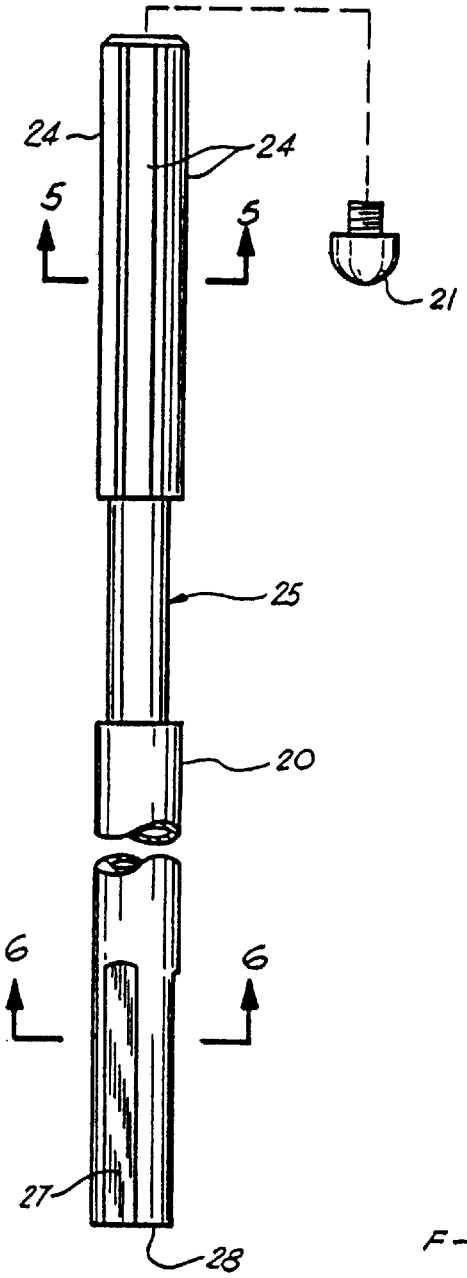
FIG. 7 is a side view of the mill portion of the apparatus of the present invention.
Figure 5:
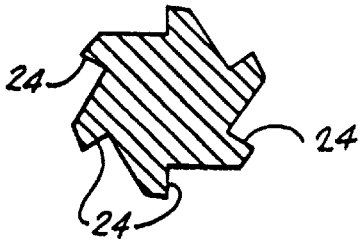
FIG. 5 is a fragmentary view of the preferred embodiment of the apparatus of the present invention illustrating the mill portion thereof.
Figure 8:
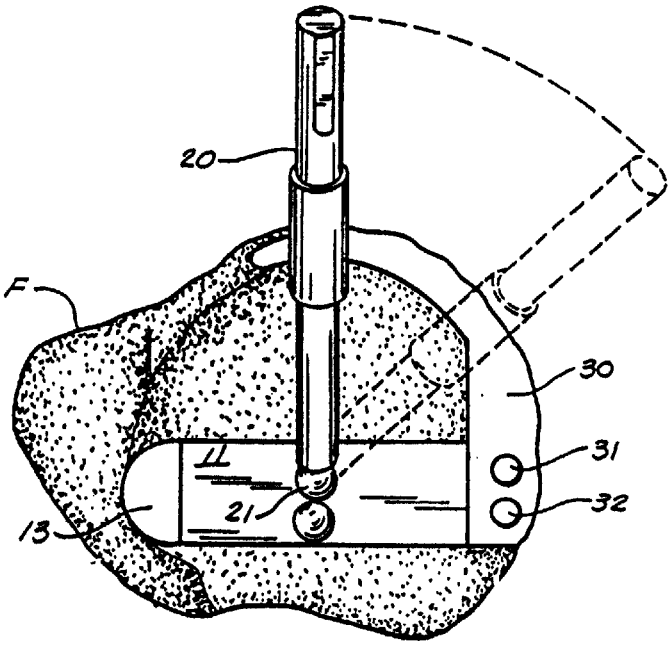
FIG. 8 is a top view of the preferred embodiment of the apparatus of the present invention, shown in position in a patient's femur with the mill being shown in hard and in phantom lines in multiple cutting positions.
Figure 9:
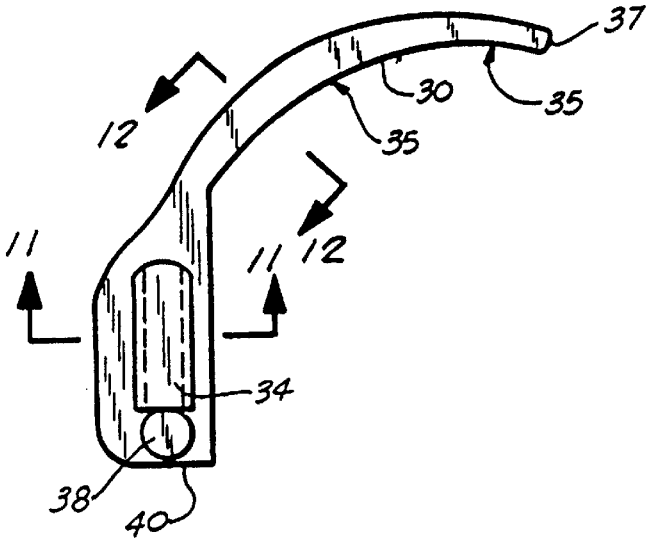
FIG. 9 is a top view of the preferred embodiment of the apparatus of the present invention illustrating a second construction of the guide rail.
Figure 11:
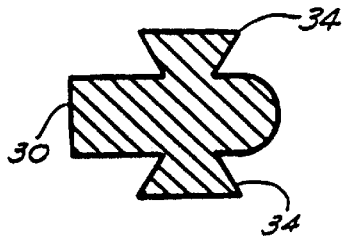
FIG. 11 is a sectional view taken along lines 11—11 of FIG. 9.
Figure 12:
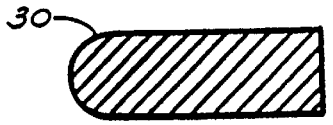
FIG. 12 is a sectional view taken along lines 12—12 of FIG. 9.
Figure 10:
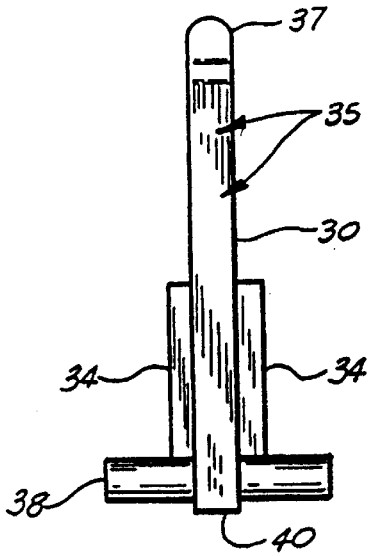
FIG. 10 is a side view of the preferred embodiment of the apparatus of the present invention showing a second construction of the guide rail.
Figure 13:
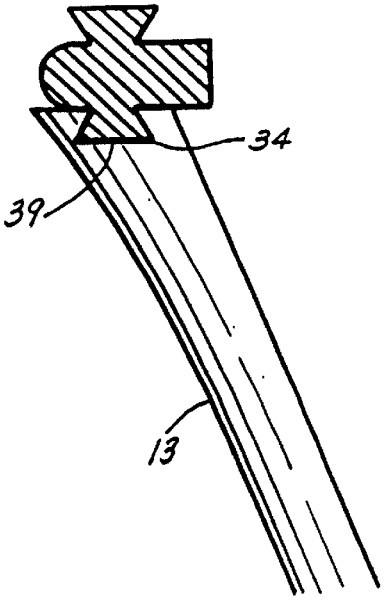
FIG. 13 is a fragmentary side view of the second construction of the guide rail connection for the embodiment of FIGS. 9–12.

FIGS. 1 and 8 show generally the preferred embodiment of the apparatus of the present invention designated generally by the numeral 10. Mill apparatus 10 includes a mill 11 having a base 12 portion at its lower end and a pair of spaced apart struts 13, 14 extending upwardly therefrom. The guide body 11 has a lower receptacle in the form of a pair of spaced apart hemispherical bearing cups 15, 16 each of which carries a corresponding hemispherical end portion 21 of reamer 20 (see FIGS. 1, 7, and 8) during use. The guide body has an overall shape and configuration, as shown in FIGS. 2 and 4, that corresponds to the shape of the upper end portion of a hip prosthesis to be implanted, so that the strut 13 defines a medial strut and the strut 14 defines a lateral strut.

The surgeon prepares the intermedullary canal with a broach, for example, which is generally shaped to the configuration of the prosthesis body to be implanted in the intermedullary canal. The broach (not shown) typically has an envelope that corresponds to the envelope of the prosthesis body to be implanted. After the surgeon prepares the intermedullary canal using the broach, the guide body 11 is inserted into the intermedullary canal and a particular guide rail 30 selected by the surgeon depending upon the shape of the desired cut to be made by the mill, and as selected by the surgeon. It is possible that cutting on one side of the guide body only would be desired, and thus the surgeon may only use the mill to cut on one side, as shown in FIG. 1.

The arm 31 would preferably be reversible in order to cut on both medial and lateral sides of the intermedullary canal. In that respect, the guide rail 30 would preferably be removable from the guide body 11, and reversible, having pairs of attachment pins 31, 32 on both its upper and its lower surfaces. Pin openings 17, 18 in guide body receive corresponding pins 31, 32 of guide rail to form the connection. In FIG. 1, the lower surface set of pins 31, 32 is not shown because the lower set of pins are in the openings 17, 18.

In the embodiment of FIGS. 9—13, a dove-tail connector 34 would be provided on each side of guide arm 30 for connecting with a corresponding dove-tailed groove 39 milled in the top of the strut 13, so that the guide rail 30 has the same generally horizontal orientation as with the preferred construction of FIG. 1. Thus, when connector 34 registers in groove 39, the rail 30 can be extended either rearwardly of guide body 11 for posterior cuts and forwardly of guide body 11 for anterior cuts. Stop pins 38 limit the movement of guide rail 30 with respect to body 11 during milling or cutting using mill.

Once attached, the guide rail 30 provides a generally curved guide surface 35 that extends between the connection end portion 40 of guide rail 30 to the free end 37 portion thereof. The shape of guide surface 35 would vary, depending upon the size of the cut to be made by the mill 20 as selected by the surgeon. Thus, a plurality of guide rails 30 could be provided in kit form to the surgeon, each with a different curvature or configuration of surface 35.

The surface 35 would be a abutted during operation with bearing sleeve 22 of mill 20, as shown in FIG. 1. The sleeve 22 could be removably attached to the central portion 23 of mill 20 which could be in the form of a reduced diameter section 25 of mill 20 as shown in FIG. 7.

Figure 6:
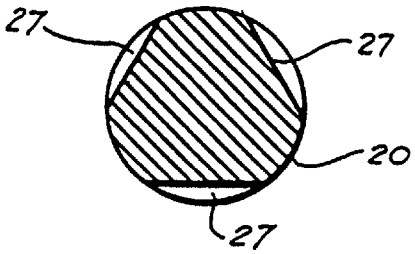
FIG. 6 is another fragmentary view of the mill portion of the apparatus of the present invention.

The upper end portion 28 of mill 20 has a tool receptive tip having multiple flat surfaces 27 which are circumferentially spaced (see FIG. 6) so that a drill or the like could be attached to drive mill 20. A plurality of circumferentially spaced apart blades 24 would be provided on the lower end of mill 20 for the purposes of cutting away bone tissue during use.

Because many varying and different embodiments may be made within the scope of the inventive concept herein taught, and because many modifications may be made in the embodiments herein detailed in accordance with the descriptive requirement of the low, it is to be understood that the details herein are to be interpreted as illustrative and not in a limiting sense.

What is claimed as invention is:

1. A guide apparatus for preparing the femur of a patient with a mill to receive a femoral hip prosthesis comprising:

a) a guide body having a lower end base, *the guide body being connectable to* [adapted to extend into the intermedullary canal of the] *a patient's* femur *during use*, and *having* an upper end portion comprised of at least one strut;

b) the [lower end of the base having] *guide body including* receptacle means for holding [one end of] a spinning mill;

c) [a] *at least a partially* curved transverse guide rail having connection means thereon for forming a connection with the upper end of the guide body, the rail having [a] *at least a partially* curved surface that is adapted to guide the mill during preparation of the [intermedullary] *intramedullary* canal of the patient's femur for receiving a hip prosthesis.

2. The apparatus of claim 1 wherein the guide body comprises a base with a pair of struts extending upwardly therefrom.

3. The apparatus of claim 2 further comprising a receptacle formed on the upper end portion of the guide body for receiving the connection means portion of the guide rail.

4. The apparatus of claim 1 wherein the connection forming means comprises a reversible connector that attached the guide rail to the guide body in multiple positions.

5. The apparatus of claim 1 wherein the guide body is V-shaped and includes medial and lateral spaced apart struts.

6. The apparatus of claim 5 wherein the connection means forms a connection with the medial strut.

7. The apparatus of claim 5 wherein the connection means comprises a receptacle carried by one of the struts of the V-shaped body, and a pair of opposed pegs carried by one end portion of the guide rail for respectively attaching the guide rail to the guide body and pre-selected left and right respective positions so that the guide rail can be used to form posterior and anterior sides of the [intermedullary] *intramedullary* canal.

8. The apparatus of claim 5 wherein the V-shaped guide body includes a pair of spaced apart struts including a generally vertically upstanding strut and inclined strut forming an acute angle therewith.

9. The apparatus of claim 5 wherein the guide body defines an envelope having a shape corresponding to the shape of an upper end portion of the prosthesis body to be placed in the patient's femur.

10. The apparatus of claim 1 wherein the receptacle means includes a pair of spaced apart, anterior and posterior receptacles each being sized to receive the lower end portion of the mill.

11. The apparatus of claim 1 wherein the guide body defines an envelope having substantially the same configuration as the prosthesis body sought to be implanted in the patient.

12. The apparatus of claim 1 wherein the guide rail includes a curved arm portion having a bearing surface thereon which allows the mill to track [and] *an* arcuate path extending generally away from the central axis of the [intermedullary] *intramedullary* canal so that the mill forms a cut in the [intermedullary] *intramedullary* canal that increases the size of the [intermedullary] *intramedullary* canal from the distal end portion thereof to the proximal end portion thereof.

13. The apparatus of claim 1 wherein the guide rail includes a cantilevered arm portion extending away from the connection means, the cantilevered arm carrying a curved guide surface that is positioned to engage the mid-section of the mill during use.

14. A guide apparatus for preparing the femur with a mill to receive a hip prosthesis comprising:

a) a V-shaped guide body having substantially the same configuration as a corresponding hip prosthesis to be implanted, said guide body including a lower end base configured to extend at least partially into the [intermedullary] *intramedullary* canal of the femur, and an upper end portion comprised of a pair of spaced apart struts forming a V-shaped configuration;

b) an elongated mill having a lower end portion with a hemispherical tip thereon and circumferentially spaced apart cutter blades extending between the hemispherical tip and at least a mid-section of the mill, and an upper end portion of the mill having a tooled end portion to receive a rotary drill for rotating the bit;

c) the lower end of the base having receptacle means for holding the end of a spinning mill bit;

d) a curved guide rail having connection means thereon for forming a connection with one of said struts, said guide rail having an arm extending substantially transverse to said struts, said arm having a curved surface that is adapted to guide the reamer bit [during] therealong as the hemispherical tip pivots in said receptacle means thereby preparing the [intermedullary] *intramedullary* canal for receipt of the hip prosthesis.

*15. A guide apparatus for preparing the femur of a patient with a mill to receive a femoral hip prosthesis, comprising:*

*a) a guide body having an upper end portion and a lower end portion, the guide body being connectable to a patient's femur, forming a connection therewith during use;*

*b) the guide body including means for holding a spinning mill during a cutting of the patient's femur at the intramedullary canal of the femur;*

*c) an at least partially curved guide rail portion that extends generally transversely with respect to the mill, the rail having means for forming a connection with the upper end portion of the guide body, the rail having a surface that is adapted to guide the mill during preparation of the intramedullary canal of the patient's femur for receiving a hip prosthesis.*

*16. A method of for preparing the femur of a patient with a mill to receive a femoral hip prosthesis, comprising the steps of:*

*a) attaching a guide body having an upper end portion and a lower end portion to the patient's femur, forming a connection therewith;*

*b) supporting a spinning mill upon the guide body during a cutting of the patient's femur at the intramedullary canal of the patient's femur;*

*c) cutting the patient's bone tissue at the intramedullary canal using the spinning mill;*

*d) guiding transverse movement of the spinning mill during cutting of the patient's bone tissue at the intramedullary canal of the patient's femur with a guide rail portion that extends generally transversely with respect to the mill, the rail being connected during use to the guide body, the rail having a surface that is adapted to guide the mill during preparation of the intramedullary canal of the patient's femur for receiving a hip prosthesis.*

*17. The method of claim 16 wherein the rail is removably attachable to the guide body.*

*18. The method of claim 17 wherein in step "a" the lower end of the guide body is attached to the patient's femur.*

*19. The method of claim 16 wherein in step "b" the mill extends partially into the patient's femur during cutting thereof.*

*20. The method of claim 16 wherein the rail prevents excess cutting of bone tissue by the mill by limiting transverse movement of the mill.*

*21. The method of claim 16, wherein the mill is generally aligned with the central longitudinal axis of the patient's intramedullary canal.*

* * * * *